United States Patent [19]

Cornelius et al.

[11] 4,418,236

[45] Nov. 29, 1983

[54] METHOD OF PRODUCING GASOLINE HYDROCARBONS FROM METHANOL

[75] Inventors: Gerhard Cornelius, Karben; Wolfgang Hilsebein, Frankfurt am Main; Helmut Ried, Karben, all of Fed. Rep. of Germany; Adolf W. Gessner, West Caldwell, N.J.

[73] Assignee: Metallgesellschaft Aktiengesellschaft, Frankfurt am Main, Fed. Rep. of Germany

[21] Appl. No.: 420,784

[22] Filed: Sep. 21, 1982

[30] Foreign Application Priority Data

Sep. 23, 1981 [DE] Fed. Rep. of Germany ....... 3137751

[51] Int. Cl.$^3$ ........................... C07C 1/20; C07C 1/22
[52] U.S. Cl. .................................... 585/408; 585/315; 585/357; 585/469; 585/639; 585/733
[58] Field of Search ..................... 585/25 M, 310, 312, 585/315, 357, 733, 638, 639, 640, 408, 409, 469

[56] References Cited

U.S. PATENT DOCUMENTS 3,998,899 12/1976 Daviduk et al. ..................... 585/314
4,044,061 8/1977 Chang et al. ........................ 585/402

*Primary Examiner*—Delbert E. Gantz
*Assistant Examiner*—A. Pal
*Attorney, Agent, or Firm*—Karl F. Ross; Herbert Dubno

[57] ABSTRACT

Gasoline hydrocarbons are produced by a catalytic conversion of methanol under a pressure of about 5 to 100 bars and at temperatures of about 250° to 500° C. The high-hydrocarbon product of the conversion is cooled so as to condense gasoline hydrocarbons. Tail gas is separated and then compressed and recycled to the conversion. In a heating step, liquid methanol is injected into a mixture of tail gas and methanol vapor and the liquid methanol is entirely evaporated. The resulting mixture of tail gas and methanol vapor is heated by about 10° to 40° C. by an indirect heat exchange with the high-hydrocarbon product. The heating step consists of the injection of liquid methanol and of the heating of the mixture of tail gas and methanol vapor and is repeated at least twice. The mixture at a temperature of about 280° to 360° C. is supplied to the catalytic conversion. Immediately before the first injection of liquid methanol, the tail gas is usually at a temperature in the range of about 60° to 120° C. The rate at which liquid methanol is injected in one heating step is preferably controlled so that the temperature of the mixture of tail gas and methanol vapor is reduced by about 10° to 40° C.

3 Claims, 2 Drawing Figures

METHOD OF PRODUCING GASOLINE HYDROCARBONS FROM METHANOL

FIELD OF THE INVENTION

This invention relates to a process for catalytically converting methanol to gasoline hydrocarbons under a pressure of about 5 to 100 bars and at temperatures in the range of about 250° to 500° C., wherein the high-hydrocarbon conversion product is cooled, gasoline hydrocarbons are condensed and a tail gas is separated and compressed and recycled to the conversion.

BACKGROUND OF THE INVENTION

Processes of this type have been disclosed in U.S. Pat. Nos. 4,011,275; 4,048,250; 4,138,442 and 4,263,141. These processes are also concerned with various possibilities of reusing the tail gas which has been separated. This is of considerable importance for the efficiency of the synthesis of the gasoline hydrocarbons.

OBJECT OF THE INVENTION

An object of the invention is to reduce the energy consumption of the process and to permit an advantageous evaporation of the liquid methanol which is to be subjected to catalytic conversion.

SUMMARY OF THE INVENTION

In the process described hereinbefore this objective is accomplished according to the invention in that in a number of heating steps a portion of the liquid methanol feed is injected into a mixture of tail gas and methanol vapor and this portion of liquid methanol is entirely evaporated, and the produced mixture of tail gas and methanol vapor is heated by about 10° to 40° C. by an indirect heat exchange with the high-hydrocarbon product. The number of these repeated heating steps is at least two. Each heating step comprises the above described injection, evaporation and heating by indirect heat exchange. Finally the mixture of tail gas and methanol vapor is fed at a temperature of about 280° to 360° C. to the catalytic conversion. In that process the heat required to evaporate the liquid methanol is entirely supplied by the cooling of the product of the catalytic conversion.

The method of catalytically converting methanol to a mixture of gasoline hydrocarbons according to the invention thus comprises the steps of:

(a) subjecting a methanol-containing gas mixture at a pressure of about 5 to 100 bar and a temperature of 250° to 500° C. to catalytic conversion in the presence of a catalyst capable of converting methanol to gasoline hydrocarbons, thereby producing a product gas mixture containing the hydrocarbons and a tail gas;

(b) cooling the product gas mixture;

(c) condensing the gasoline hydrocarbons from the cool product gas mixture and separating the tail gas therefrom;

(d) injecting a liquid portion of the methanol feed required in step (a) into at least a portion of the tail gas separated in step (c) to thereby completely evaporate the injected methanol and form a mixture of tail gas and methanol vapor;

(e) heating the mixture of tail gas and methanol vapor by about 10° to 40° C. in indirect heat exchange with the product gas mixture;

(f) injecting one further portion of liquid methanol into the heated mixture of tail gas and methanol vapor to fully vaporize the additionally injected methanol therein and produce an enriched mixture further enriched in methanol vapor;

(g) heating said enriched mixture by about 10° to 40° C. in indirect heat exchange with said product gas mixture;

(h) repeating steps (f) and (g) at least once with another portion and finally with the balance of the liquid methanol to produce a final mixture containing all the methanol feed; and (i) introducing the final mixture at a temperature of 280° to 360° C. into step (a) to thereby produce the methanol feed for the catalytic conversion.

For a rapid heat transfer it is important in the process according to the invention that the temperature difference between the high-hydrocarbon product and the mixture of tail gas and methanol vapor during the indirect heat exchange in the heating steps is about 20° to 60° C. This permits the heat exchange to be effected in equipment having small dimensions.

The rate at which liquid methanol is injected into a heating step is preferably so controlled that the temperature of the mixture of tail gas and methanol vapor is reduced by about 10° to 40° C. The indirect heat exchange between the mixture and the high-hydrocarbon product within one heating step preferably results in a temperature rise of the mixture also of about 10° to 40° C.

The temperature of the mixture of tail gas and methanol vapor does not rise or rises only slightly from heating step to heating step and the heat supplied to the mixture is used substantially only to evaporate the injected methanol. The number of heating steps required to evaporate all of the methanol feedstock may vary and amounts to at least 3 and preferably to 4 to about 10 heating steps, in these numbers the first step with injection of the first portion of liquid methanol into the tail gas still free from methanol vapor is included.

The temperatures of the different mixtures of tail gas and methanol vapor lie in the range of about 65° to 100° C. until all of the liquid methanol feedstock has been evaporated into the mixture. Another indirect heat exchange with the high-hydrocarbon product of the conversion is subsequently required in order to heat the mixture to the inlet temperature of the converter; that inlet temperature is preferably at least 300° C.

BRIEF DESCRIPTION OF THE DRAWING

The above and other objects, features and advantages of the present invention will become more readily apparent from the following description, reference being made to the accompanying drawing in which.

SPECIFIC DESCRIPTION

Figure 1:
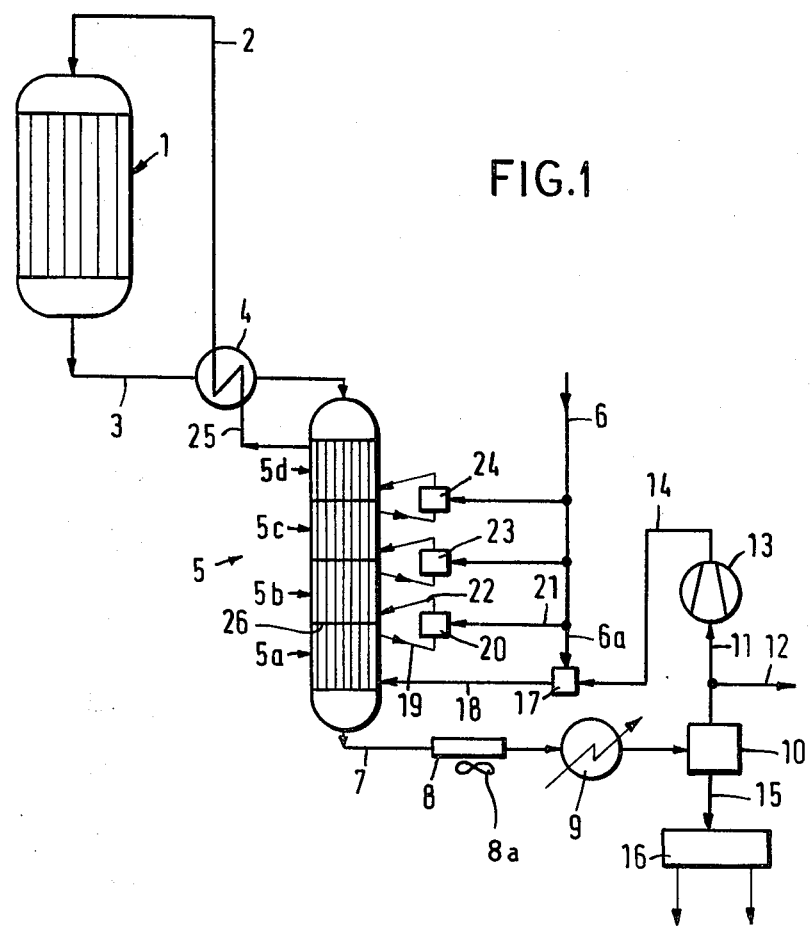
FIG. 1 is a flow diagram illustrating the invention.

In FIG. 1 we have shown a catalytic reactor 1 in which the conditions are maintained for the catalytic conversion of methanol to gasoline hydrocarbons. This catalytic converter is thus capable of maintaining a pressure of 5 to 100 bar at a temperature of 250° to 500° C. and contains a zeolite or other catalyst suitable for conversion.

At a temperature preferably of about 280° to 360° C., a mixture of methanol vapor and tail gas is supplied in conduit 2 to the reactor 1. The tail gas consists mainly of low-boiling hydrocarbons and the inert constituents $CO_2$, $N_2$ and Ar. The known catalytic conversion to a high-hydrocarbon product and water vapor is effected in the reactor 1, which is usually indirectly cooled. For this reason the catalyst, which may consist of known zeolites, may be arranged in tubes which are indirectly cooled by molten salts. But the process according to the invention is not restricted to a specific design of the reactor 1.

The high-hydrocarbon product leaves the reactor 1 through conduit 3 at temperatures in the range of about 300° to 500° C. and is indirectly cooled for the first time in the heat exchanger 4 with the mixture from conduit 25. By the subsequent cooling in the cooler 5, the liquid methanol supplied in conduit 6 is evaporated entirely. Details of that evaporation will be explained hereinafter.

The high-hydrocarbon product leaves the cooler 5 in conduit 7 and usually has a temperature in the range of about 60° to 120° C. That product is then air-cooled in a cooler 8 and water-cooled in a cooler 9, which is succeeded by a separator 10. Tail gas leaves the separator through conduit 11 and surplus gas can be withdrawn through conduit 12. The remaining residual gas is compressed in the compressor 13 and is then fed to the cooler 5 in conduit 14. A mixture of gasoline and water is supplied in conduit 15 to a separator 16 and is separated therein.

Methanol is supplied to conduit 6 from a supply tank, not shown, or directly from a methanol synthesizer. The liquid methanol in conduit 6 may contain up to about 20% water. A partial stream of that methanol, e.g. 10 to 50% thereof, is injected through conduit 6a into the mixing chamber 17, which is supplied with tail gas from conduit 14. The methanol injected into the mixing chamber 17 is entirely evaporated. Owing to the work of compression supplied by the compressor 13, the tail gas in conduit 14 normally is at a temperature of about 60° to 120° C.; that tail gas is cooled by the latent heat of evaporation of the partial stream of methanol which is injected into the mixing chamber 17. The resulting mixture of tail gas and methanol vapor is delivered by conduit 18 to the product cooler 5. The cooler 5 outside the tubes containing product from reactor 1 is divided into a plurality of sections by 3 partitions 26 so that another quantity of liquid methanol can be injected into the mixture of tail gas and methanol vapor when the mixture has been subjected to a relatively small temperature rise of about 10° to 40° C.

An embodiment of the cooler 5 is shown in FIG. 1, which is intended to illustrate also the principle of the evaporation of the methanol. In that embodiment, a conduit 19 supplies the mixture of tail gas and methanol vapor from the top of the lowermost cooler section 5a to a mixing chamber 20, which is disposed outside the cooler 5 and in which another portion, e.g. 10 to 35%, of the liquid methanol supplied in conduit 6, is injected from conduit 21. In that operation, care is also taken that the injected methanol is completely evaporated. As a result, the temperature of the mixture is reduced by about 10° to 40° C. The resulting mixture is delivered in conduit 22 to the next cooler section 5b and is reheated therein. Adjacent cooler section are separated by a partition 26. The stepwise evaporation and heating are repeated in the next cooler sections 5c and 5d having mixing chambers 23 and 24 associated therewith. It is apparent that each heating step comprises the injection of liquid methanol into a mixture of tail gas and methanol vapor (only tail gas comes from conduit 14) and the resulting cooling as well as the subsequent reheating by an indirect heat exchange with the high-hydrocarbon product in the cooler 5. In the last heating step the remaining liquid methanol is evaporated and the resulting mixture leaving the cooler 5 through conduit 25 is at a temperature of about 70° to 150° C. The mixture is heated further by an indirect heat exchange in the heat exchange 4 and is delivered in conduit 2 to the reactor 1.

Figure 2:
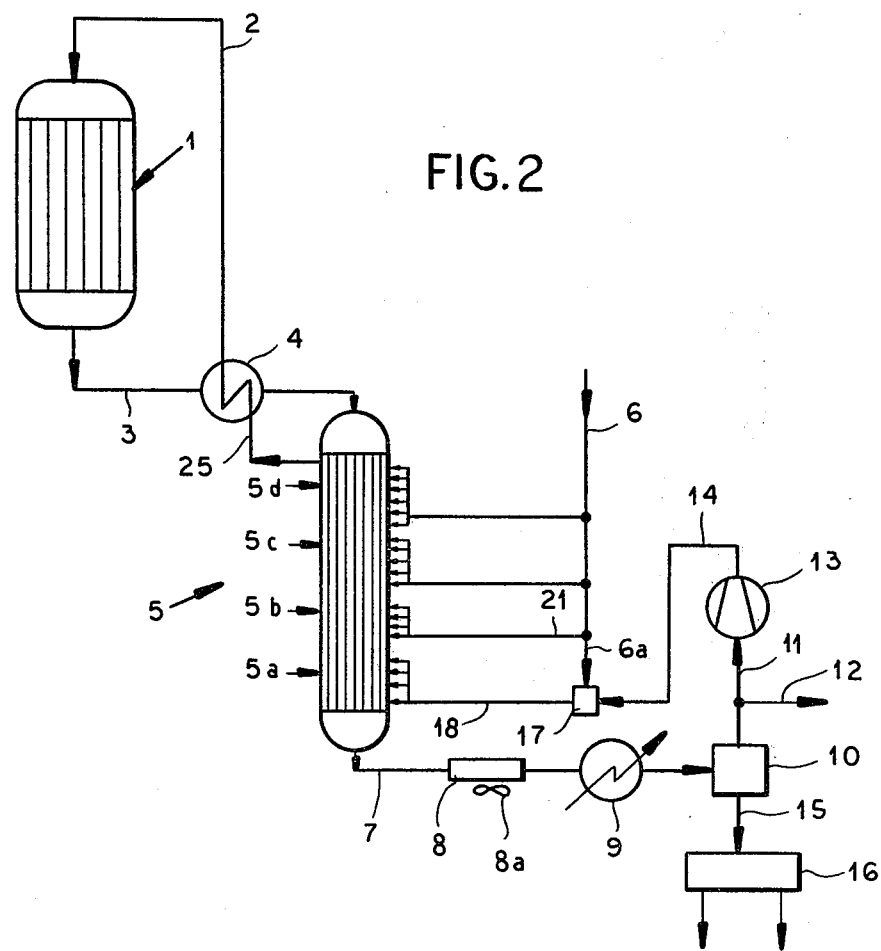
FIG. 2 is another flow diagram showing a modification thereof.

The embodiment shown in FIG. 1 may be modified in that no external mixing chambers 20, 23 and 24 are associated with the cooler 5 and according FIG. 2 the portions of liquid methanol are injected through manifolds 20a, 23a and 24a within the cooler 5 into the mixture contained in the cooler. In that case (FIG. 2) there are no partitions between cooler sections and the manifolds 20a, 23a and 24a may be installed at the places where the partitions 26 of FIG. 1 are. In another alternative, each cooler section may constitute a separate cooler provided with built-in or externally disposed means for injecting the liquid methanol into the mixture.

EXAMPLE

A system in FIG. 1 of the drawing is operated as follows: 1000 kg liquid methanol at 30° C. are supplied through conduit 6 to mixing chambers 17, 20, 23 and 24. 6296 $m^3$ (N.T.P.) tail gas are at 80° C. and 14 bars as they enter the mixing chamber 17 from conduit 14. 367 kg liquid methanol are injected into the mixing chamber so that the mixture assumes a temperature of 50° C. and the methanol is entirely evaporated.

The mixture of tail gas and methanol vapor flows through conduit 18 to the shell part of the cooler 5. The mixture is heated to 70° C. in the bottom section 5a and then flows to the mixing chamber 20, in which 211 kg methanol are injected from conduit 21. As a result, the temperature of the mixture of tail gas and methanol vapor is reduced to 55° C. and the methanol is entirely evaporated. The resulting mixture is heated to 73° C. in cooling section 5b. That operation is repeated in mixing chambers 23 and 24 and in cooling sections 5c and 5d. After flowing through the uppermost section 5d of the cooler 5, the mixture leaves the cooler at 80° C. and is supplied in conduit 25 to the heat exchanger 4.

The mixture of tail gas and methanol vapor is heated to about 340° C. in the heat exchanger 4 and is then fed through conduit 2 into the reactor 1, where the mixture is catalytically converted. As a result, the temperature rises to about 380° C. The high-hydrocarbon product is cooled to 120° in the heat exchanger 4 and then flows to the tube part of the cooler 5. A pressure of about 10 bars is obtained in the shell and tube parts of the cooler section 5d.

A mixture of gas, water and hydrocarbons is at about 85° C. as it leaves the cooler 5 and is delivered in conduit 7 to the air-cooled condenser 8, where it is cooled to about 60° C., and subsequently to the water-cooled condenser 9, where it is cooled to about 30° C. Water and hydrocarbons at substantial rates are condensed during these cooling steps.

The two liquid fractions consisting of water and hydrocarbons are separated from the tail gas in the separator 10 and are separated from each other in the separator 16. The tail gas is conducted in conduit 11, from which a partial stream is withdrawn in conduit 12. The remaining tail gas in conduit 11 is compressed to about 14 bars by the compressor 13 and is then supplied at about 80° C. to the means for evaporating methanol.

For comparison, in a conventional process liquid methanol under a pressure of 14 bars is first preheated from 30° to 140° C. and is then transferred into vapor at 14 bars and 140° C. That vapor is supplied to the tail gas, which is also under a pressure of 14 bars and is at a temperature of 100° C., to which the tail gas had previously been heated in a heat exchanger which corresponds to the cooler 5. A major part of the high-hydrocarbon product cannot be used to preheat and evaporate the methanol because that heat has been used to preheat the tail gas. The mixture of tail gas and methanol vapor is heated in the heat exchanger by an indirect heat exchange with the high-hydrocarbon product to the inlet temperature of reactor 1. In the present case, extraneous energy is required to preheat and evaporate the liquid methanol because the temperature of the product coming from the indirect heat exchange with the tail gas is not sufficient for use in evaporating the methanol.

We claim:

1. A method of catalytically converting methanol to a mixture of gasoline hydrocarbons comprising the steps of:
   (a) subjecting a methanol-containing gas mixture at pressure of about 5 to 100 bar and a temperature of 250° to 500° C. to catalytic conversion in the presence of a catalyst capable of converting methanol to gasoline hydrocarbons, thereby producing a product gas mixture containing said hydrocarbons and a tail gas;
   (b) cooling said product gas mixture;
   (c) condensing said gasoline hydrocarbons from the cool product gas mixture and separating said tail gas therefrom;
   (d) recovering from step (c) at least a portion of separated tail gas at a temperature of substantially 60° to 120° C. and injecting a liquid portion of 10 to 50% of the methanol feed required in step (a) into the recovered tail gas separated in step (c) and at said temperature of substantially 60° to 120° C. to thereby completely evaporate the injected methanol and form a mixture of tail gas and methanol vapor;
   (e) heating said mixture of tail gas and methanol vapor by about 10° to 40° C. in indirect heat exchange with said product gas mixture by maintaining the temperature differential between said product gas mixture and the mixture of tail gas and methanol vapor at about 20° to 60° C.;
   (f) injecting one further portion of liquid methanol into the heated mixture of tail gas and methanol vapor to fully vaporize the additionally injected methanol therein and produce an enriched mixture further enriched in methanol vapor, and heating said enriched mixture by about 10° to 40° C. in indirect heat exchange with said product gas mixture by maintaining the temperature differential between said product gas mixture and the mixture of tail gas and methanol vapor of about 20° to 60° C.;
   (g) repeating step (f) at least once with another portion and finally with the balance of the liquid methanol to produce a final mixture at a temperature of substantially 70° to 150° C. containing all the methanol feed, the quantity of each injected portion of liquid methanol being selected to reduce the temperature of the resulting mixture of tail gas and methanol vapor by substantially 10° C. to substantially 40°; and
   (h) heating the final mixture by indirect heat exchange with said product gas to a temperature of 280° to 360° C. and thereupon introducing said final mixture into step (a) to thereby provide the methanol feed for the catalytic conversion.

2. The method defined in claim 1 wherein, during indirect heat exchange and product gas mixture is passed in counterflow to the mixtures of tail gas and methanol vapor.

3. The method defined in claim 1 wherein the liquid methanol is injected into the tail gas or a mixture of tail gas and methanol vapor outside the zone of indirect heat exchange.

* * * * *